(12) United States Patent
Kubota et al.

(10) Patent No.: US 6,984,532 B2
(45) Date of Patent: Jan. 10, 2006

(54) METHOD OF JUDGING RESIDUAL FILM BY OPTICAL MEASUREMENT

(75) Inventors: Takeo Kubota, Kawasaki (JP); Atsushi Shigeta, Fujisawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 184 days.

(21) Appl. No.: 10/396,310

(22) Filed: Mar. 26, 2003

(65) Prior Publication Data

US 2003/0197859 A1    Oct. 23, 2003

(30) Foreign Application Priority Data

Mar. 27, 2002 (JP) ............................. 2002-089775

(51) Int. Cl.
*H01L 21/66* (2006.01)

(52) U.S. Cl. ................. 438/14; 438/15; 438/16; 438/17; 438/687; 356/381; 356/382

(58) Field of Classification Search ............... 438/14, 438/15, 16, 17, 687; 451/5, 6; 356/381, 356/382
See application file for complete search history.

(56) References Cited

U.S. PATENT DOCUMENTS

| | | | | |
|---|---|---|---|---|
| 5,166,080 A | * | 11/1992 | Schietinger et al. | ........... 438/7 |
| 5,499,733 A | | 3/1996 | Litvak | |
| 6,204,922 B1 | * | 3/2001 | Chalmers | ..................... 356/630 |
| 6,306,669 B1 | | 10/2001 | Yano et al. | |
| 6,309,555 B1 | * | 10/2001 | Chen | ........................... 216/85 |
| 6,658,144 B1 | * | 12/2003 | Hatab | ........................ 382/144 |
| 6,750,143 B1 | * | 6/2004 | Iijima et al. | ................ 438/678 |
| 6,753,249 B1 | * | 6/2004 | Chen et al. | ................. 438/637 |
| 2001/0039064 A1 | * | 11/2001 | Ushio et al. | ................. 438/14 |
| 2003/0207476 A1 | * | 11/2003 | Eriguchi et al. | .............. 438/16 |

FOREIGN PATENT DOCUMENTS

JP          11-325840         11/1999

* cited by examiner

*Primary Examiner*—W. David Coleman
*Assistant Examiner*—Victor V. Yevsikov
(74) *Attorney, Agent, or Firm*—Finnegan, Henderson, Farabow, Garrett & Dunner, L.L.P.

(57) ABSTRACT

A method of judging a residual film on a sample by an optical measurement, the sample including a first metal film whose reflectance is changed depending on a wavelength of measuring light, and an insulating film formed above the first metal film, and the residual film being a second metal film above the insulating film, the method comprising irradiating the sample with a measuring light so as to measure a change in intensity of light reflected from the sample depending on the wavelength of the measuring light, thereby obtaining a reflectance spectrum curve, and dividing the reflectance spectrum curve into a plurality of wavelength regions so as to judge presence or absence of the second metal film above the insulating film depending on a waveform in each of the wavelength regions of the reflectance spectrum curve.

18 Claims, 7 Drawing Sheets

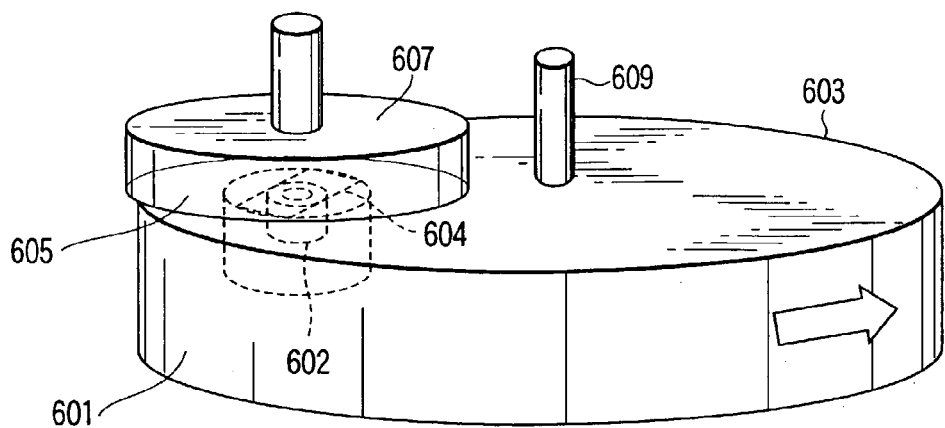
F I G. 6A
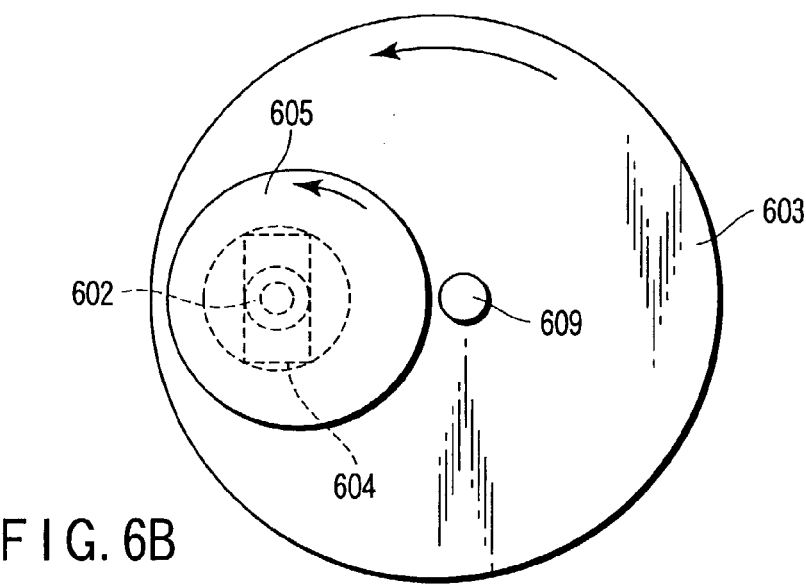
F I G. 6B
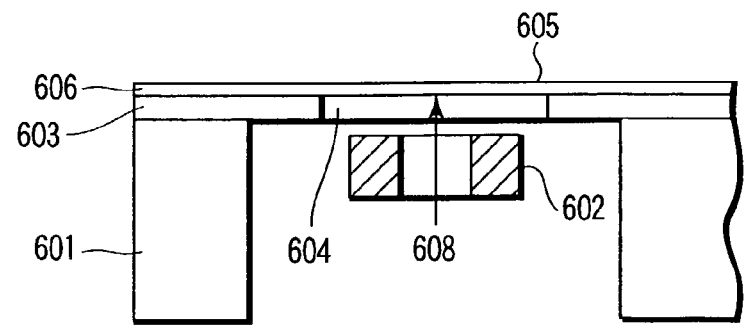
F I G. 6C

METHOD OF JUDGING RESIDUAL FILM BY OPTICAL MEASUREMENT

CROSS-REFERENCE TO RELATED APPLICATIONS

This application is based upon and claims the benefit of priority from the prior Japanese Patent Application No. 2002-089775, filed Mar. 27, 2002, the entire contents of which are incorporated herein by reference.

BACKGROUND OF THE INVENTION

1. Field of the Invention

The present invention relates to a method of judging a residual film by an optical measurement, particularly, to a method of judging a residual film by means of a spectral reflection interferometer in the inspecting step involved in the manufacturing process of a semiconductor device.

2. Description of the Related Art

In the conventional method of measuring a film thickness by using a spectral reflection interferometer, fitting is performed between the measured reflectance spectrum and the reflection spectrum calculated from an expected model of a stacked film so as to determine the film thickness, thereby judging the laminate structure of a sample. In the conventional method, however, the fitting becomes poor if the structure of the film to be measured differs from that of the optical model used for the film thickness calculation, with the result that it is possible for the judgment to be erroneous.

In CMP of a Cu film, which is carried out for forming a Cu damascene wiring over a Cu buried wiring with an interlayer insulating film interposed therebetween, a Cu film and a barrier metal (BM) film are polished so as to remove completely the Cu film and the barrier metal (BM) film in a field portion other than the wiring section while allowing the Cu film and the barrier metal (BM) film to be left unremoved in the wiring section alone. Therefore, under the state that the Cu film is left unremoved, the residual film in the field portion has a stacked structure of a Cu film/BM film/interlayer insulating film/Cu buried wiring. It follows that it is necessary to carry out the film thickness calculation while changing the thickness of each of at least the Cu film, the BM film and the interlayer insulating film, leading to the requirement of a tremendous calculation amount.

Such being the situation, it is conceivable to decrease the calculation amount by dividing the situation into several cases as follows depending on the CMP treatment.

Specifically, the state of the field portion can be classified into at least the three states given below:

a) Presence of a Cu residual film (NG—additional polishing);

b) Presence of a BM residual film (NG—additional polishing);

c) No residual film (finish OK)

It is conceivable to classify the state of the field portion into the three states given above and to carry out the film thickness calculation while changing the thickness of each of the uppermost layer and the layer immediately below the uppermost layer. In this method, however, it is necessary to carry out the film thickness calculation by assuming the construction of each of the layers, and it is difficult to classify the state into suitable cases. Under the circumstances, a simpler method is required for judging the residual film in the field portion.

BRIEF SUMMARY OF THE INVENTION

According to an aspect of the present invention, there is provided a method of judging a residual film on a sample by an optical measurement, the sample including a first metal film whose reflectance is changed depending on a wavelength of measuring light, and an insulating film formed above the first metal film, and the residual film being a second metal film above the insulating film, the method comprising: irradiating the sample with a measuring light so as to measure a change in intensity of light reflected from the sample depending on the wavelength of the measuring light, thereby obtaining a reflectance spectrum curve; and dividing the reflectance spectrum curve into a plurality of wavelength regions so as to judge presence or absence of the second metal film above the insulating film depending on a waveform in each of the wavelength regions of the reflectance spectrum curve.

According to another aspect of the present invention, there is provided a method of judging a residual film by an optical measurement for judging presence or absence of a barrier film and a metal film above an insulating film of a semiconductor substrate provided with a Cu wiring and the insulating film formed above the Cu wiring, comprising: irradiating a surface of the semiconductor substrate above the Cu wiring with a measuring light so as to measure a change in intensity of light reflected from the semiconductor substrate depending on a wavelength of the measuring light, thereby obtaining a reflectance spectrum curve; and dividing the reflectance spectrum curve into a plurality of regions including a wavelength region on a side of a short wavelength not longer than 500 nm and a wavelength region on a side of a long wavelength not shorter than 650 nm so as to judge any of three states on the insulating film including (a) substantially presence of the metal film, (b) substantially absence of the metal film and presence of the barrier film, and (c) absence of the metal film and absence of the barrier film, by allowing presence or absence of a periodic wave, or amplitude of the periodic wave on the side of each of the short wavelength and the long wavelength in the reflectance spectrum curve to correspond to the three states given above.

Further, according to still another aspect of the present invention, there is provided a method of manufacturing a semiconductor device, comprising: providing a semiconductor substrate including a first metal film whose reflectance is changed depending on the wavelength of a measuring light and an insulating film formed above the first metal film; depositing a second metal film above the insulating film; removing selectively the second metal film from a surface of the second metal film gradually; irradiating a prescribed region of the semiconductor substrate with a measuring light so as to measure a change in intensity of light reflected from the semiconductor substrate depending on the wavelength of the measuring light, thereby obtaining a reflectance spectrum curve; and dividing the reflectance spectrum curve into a plurality of wavelength regions so as to judge presence or absence of the second metal film above the insulating film in a prescribed region depending on waveform of the reflectance spectrum curve in each of wavelength regions, thereby detecting an end point in removal of the second metal film, wherein the removal of the second metal film is stopped based on the detected end point so as to finish removing the second metal film.

BRIEF DESCRIPTION OF THE SEVERAL VIEWS OF THE DRAWING

FIGS. 6A to 6C collectively show the construction of an in-situ reflectance measuring apparatus for measuring the reflectance during the CMP treatment applied to a Cu film in Example 2 of the present invention;

DETAILED DESCRIPTION OF THE INVENTION

Figure 1A:
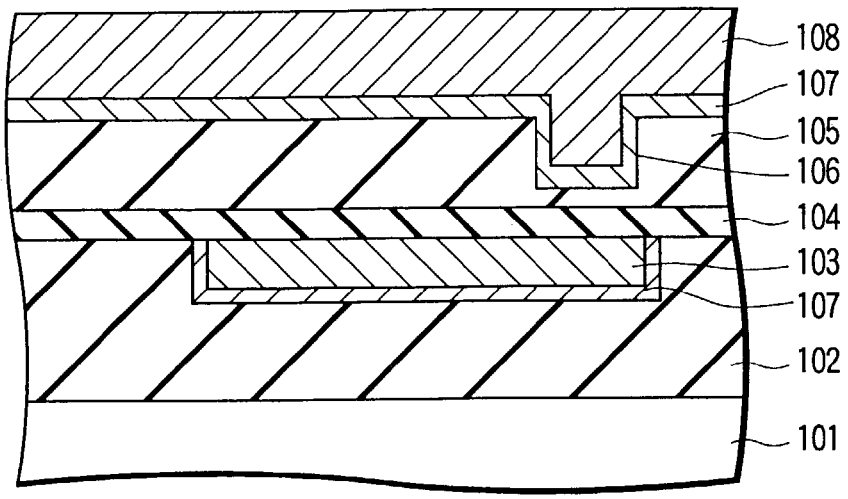
FIGS. 1A to 1C are cross-sectional views collectively showing the process of forming a Cu damascene wiring in Example 1 of the present invention.

Some embodiments of the present invention will now be described.

As a result of extensive research conducted on the method of judging by an optical measurement the residual film in the polishing step, the present inventors paid attention to the situation that, since the polishing is insufficient in the case where the polishing residual film is present in the field portion, judgment on only the presence or absence of the polishing residual film is required for the judgment on the necessity of, for example, additional polishing, and the thickness of the polishing residual film in the field portion is not necessarily required information.

The method of judging the residual film by an optical measurement according to a first embodiment of the present invention, which is based on the particular situation described above, comprises measuring the change in the intensity of light reflected from a sample depending on the wavelength of the measuring light so as to obtain a reflectance spectrum curve, and dividing the reflectance spectrum curve into a plurality of wavelength regions so as to judge presence or absence of a second metal film on an insulating film formed on a first metal film depending on the waveform of the reflectance spectrum curve in each of the wavelength regions.

In the method according to the first embodiment of the present invention, the presence or absence of the second metal film on the insulating film is judged by only the amplitude of the reflectance spectrum curve divided depending on the wavelength of light reflected from the sample, with the result that the polishing residual film can be judged easily and in a short time while eliminating the necessity in the prior art for measuring the thickness of the residual film.

To be more specific, in the method of judging the residual film according to the first embodiment of the present invention, the presence or absence of the second metal film on the insulating film is judged by allowing the presence or absence of the periodic wave, or the amplitude of the periodic wave in each of the wavelength regions of the reflectance spectrum curve to correspond to the presence or absence of the second metal film on the insulating film.

In this case, it is desirable for the first metal to be a metal whose reflectance is rapidly changed depending on the wavelength of the measuring light. To be more specific, it is desirable for the first metal to be a colored metal such as Cu or Au. It is desirable for the first metal layer to be thick enough to prevent the measuring light from being transmitted therethrough. For example, the thickness of the first metal layer may be at least about 100 nm.

Also, in the method of judging the residual film by an optical measurement according to the first embodiment of the present invention, it is possible for a Cu wiring to constitute the first metal film and for a metal film forming an underlying barrier film to constitute the second metal film. It is possible for the judging method according to the first embodiment of the present invention to be employed for the judgment on the presence or absence of these barrier film and metal film on an insulating film.

In this case, the reflectance spectrum curve is divided into a plurality of regions including a region on the side of a short wavelength not longer than 500 nm and a region on the side of a long wavelength not shorter than 650 nm. It is possible to judge any of the three states including (a) the presence of a thick metal film, (b) the presence of a thin metal film and a barrier film, or the absence of a metal film and the presence of a barrier film, and (c) the absence of a metal film and a barrier film, by allowing the presence or absence, or the amplitude of the periodic wave on the side of the short wavelength and on the side of the long wavelength in the reflectance spectrum curve to correspond to the three states (a) to (c) noted above.

To be more specific, where the periodic wave on any of the short wavelength side and the long wavelength side in the reflectance spectrum curve is not present or the amplitude of that periodic wave is small, it is judged that the situation on the insulating film is under state (a) given above. Where the periodic wave on each of the short wavelength side and the long wavelength side in the reflectance spectrum curve is present or the amplitude of that periodic wave is large, it is judged that the situation on the insulating film is under state (b) given above. Further, where the periodic wave on the short wavelength side in the reflectance spectrum curve is present or the amplitude of that periodic wave is large, and the periodic wave on the long wavelength side in the reflectance spectrum curve is not present or the amplitude of that periodic wave is small, it is judged that the situation on the insulating film is under state (c) given above.

As described above, the residual film can be judged based on only two wavelength regions of the reflectance spectrum curve so as to make it possible to judge the residual film easily and in a short time.

In the method according to the first embodiment of the present invention, it is possible for the insulating film to be a film selected from the group consisting of a silicon oxide film, a silicon nitride film, a silicon oxide film to which at least one of fluorine, phosphorus and boron is added, an organic insulating film, and a laminated film including some of these insulating films. It is desirable for the insulating film to be formed of a material low in absorption of light having a wavelength falling within a range of the wavelengths of the measuring light components and substantially transparent to light and to have a thickness large enough to generate interference accompanying the wavelength. For example, it is desirable for the insulating film to have a thickness of 0.2 to 2 μm.

On the other hand, it is possible for the barrier film to be a film selected from the group consisting of a tantalum film, a tantalum nitride film, a titanium film, a titanium nitride film, a tungsten film, a tungsten nitride film, and a laminated film including some of these barrier films. It is desirable for the barrier film to have a thickness that permits transmitting light having a wavelength range of the measuring light. For example, it is desirable for the barrier film to have a thickness of 50 nm or less.

In another embodiment of the present invention, the method of judging the residual film by an optical measurement is applied to the manufacturing method of a semiconductor device utilizing the detection of the end point of the removal of the second metal film.

The second metal film can be removed by, for example, a CMP (Chemical Mechanical Polishing) method or a RIE (Reactive Ion Etching) method. Particularly, the method of judging the residual film by an optical measurement can be effectively utilized for detecting the end point of the CMP treatment in the case where a metal film is buried using the CMP treatment in at least one of a groove and a hole formed in an insulating film.

To be more specific, it is possible to detect the end point of the polishing easily and in a short time in depositing a second metal film in a manner to fill at least one of a groove and a hole made in an insulating film, followed by polishing the deposited second metal film so as to permit the residual second metal film to be buried in at least one of the groove and the hole while removing that portion of the deposited second metal film which is positioned on the insulating film on the outside of the groove and the hole.

Various Examples of the present invention will now be described with reference to the accompanying drawings.

EXAMPLE 1

The formation of a laminate structure of a Cu damascene wiring will now be described with reference to FIG. 1. As shown in FIG. 1A, an insulating film 102 is formed on the surface of a semiconductor substrate 101 having active elements (not shown) formed therein. Also, a Cu buried wiring 103 is formed in the insulating film 102 with a tantalum nitride (TaN) liner film 107 interposed between the Cu buried wiring 103 and the insulating film 102. Further, a silicon nitride (SiN) film 104 and a silicon dioxide (SiO$_2$) film 105 acting as an interlayer insulating film are successively formed on the resultant structure.

Figure 1B:
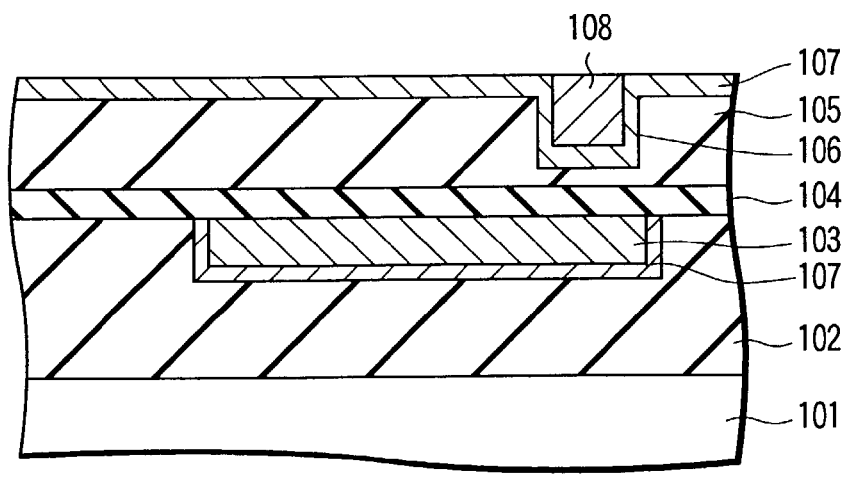
Figure 1C:
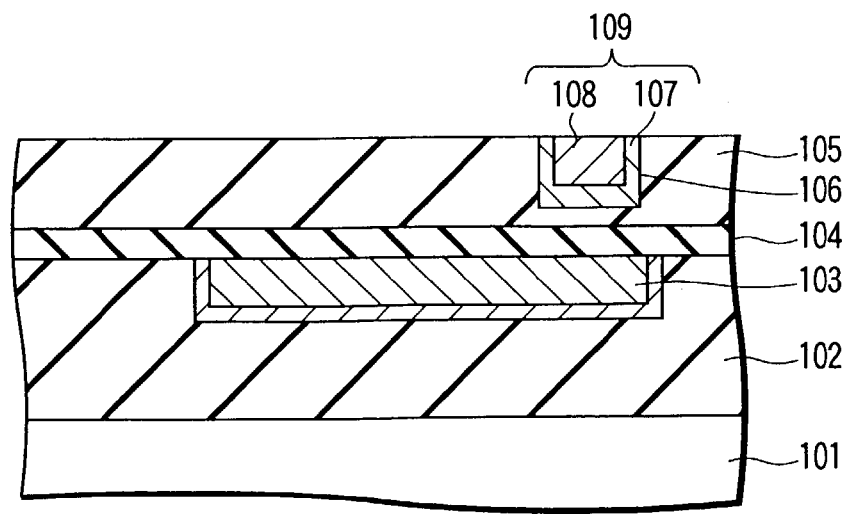

In the next step, a wiring groove 106 and a hole (not shown) for forming a plug serving to connect electrically the lower wiring layer to the upper wiring layer are formed in the interlayer insulating film 105, following by forming a laminate structure of a tantalum nitride (TaN) liner film 107 and a copper (Cu) film 108 in a manner to fill the wiring groove 106. After formation of the laminate structure noted above, those regions of the copper (Cu) film 108 and the tantalum nitride (TaN) liner film 107 which are positioned on the field portion (outside the wiring groove 106) are removed by the CMP (Chemical Mechanical Polishing) method so as to permit the films 108 and 107 to remain unremoved within the wiring groove 106, thereby forming a Cu buried wiring 109, as shown in FIGS. 1B and 1C.

In this case, the situation above the field portion of the interlayer insulating film 105 is changed in three stages given below in accordance with the progress of the polishing by the CMP treatment:

a) The stage in which the Cu film 108 remains substantially unremoved;

b) The stage in which the Cu film 108 is substantially eliminated and the TaN film 107 remains unremoved;

c) The stage in which both the Cu film 108 and the TaN film 107 are eliminated.

Figure 2:
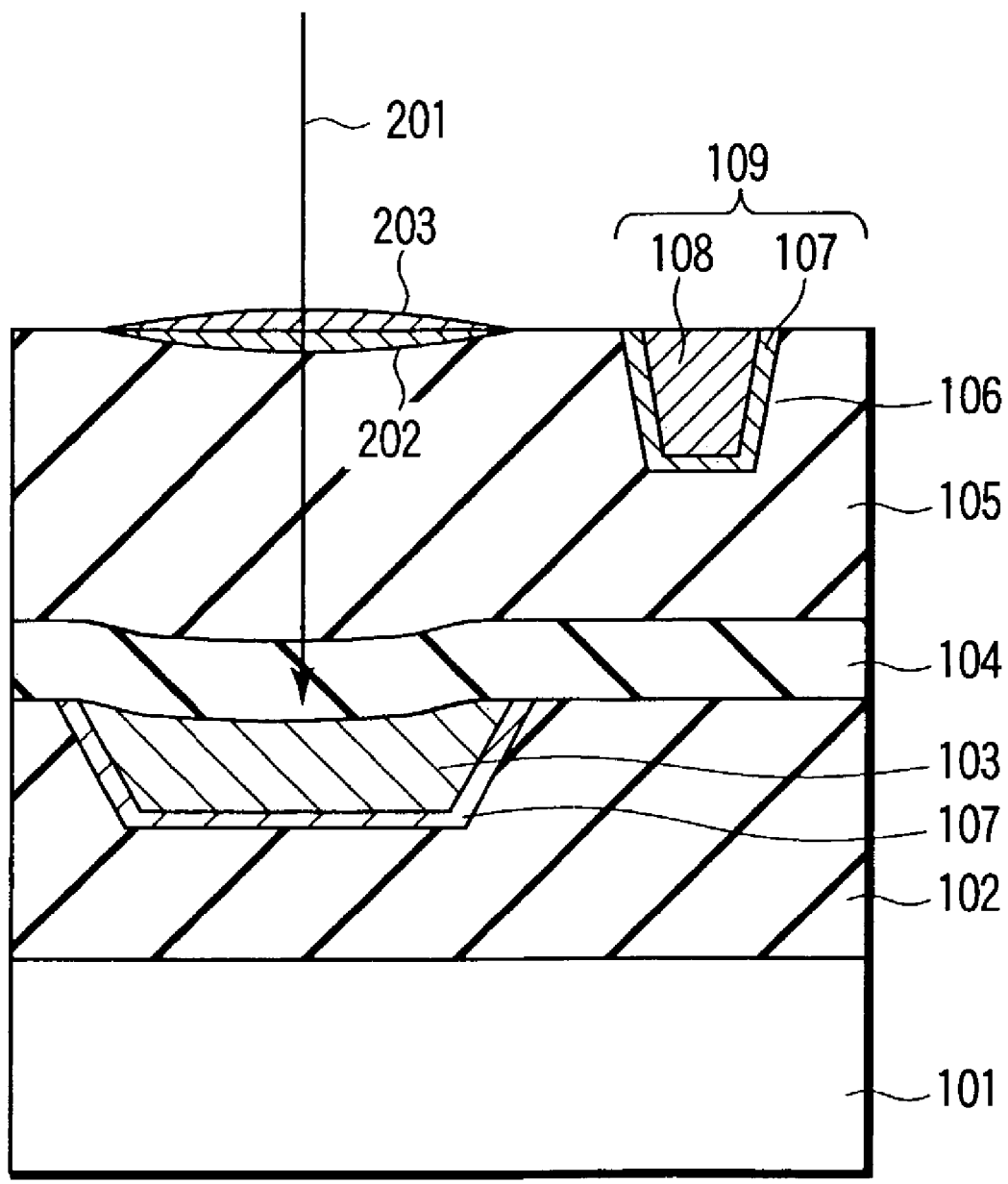
FIG. 2 is a cross-sectional view for explaining the judgment of the residue of the metal film in forming the Cu damascene wiring in Example 1 of the present invention.

FIG. 2 shows how the field portion of the interlayer insulating film 105 is irradiated with light 201 during the CMP treatment so as to measure the reflectance. The reflectance is measured by changing the wavelength within a range of between 300 nm and 800 nm. Incidentally, a large dishing is formed on the Cu wiring 103 having a large width of scores of microns, to which an optical measurement can be applied, and a residual film 202 of the TaN film 107 and a residual film 203 of the Cu film 108 tend to be generated above the dished portion. Therefore, the region above the Cu wiring 103 is adapted for monitoring the residual film after the CMP treatment.

Figure 3A:
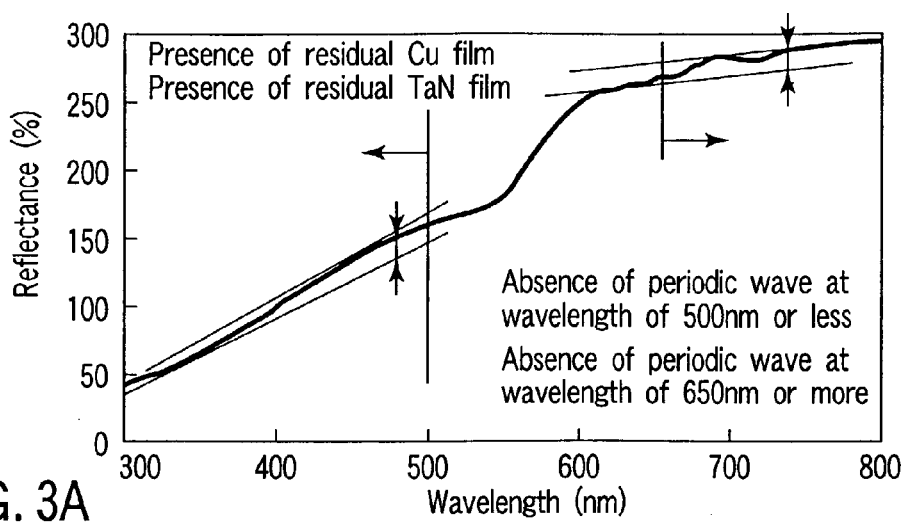
FIGS. 3A to 3C are graphs each showing the reflectance spectrum that is changed with progress of the CMP treatment in Example 1 of the present invention.
Figure 3B:
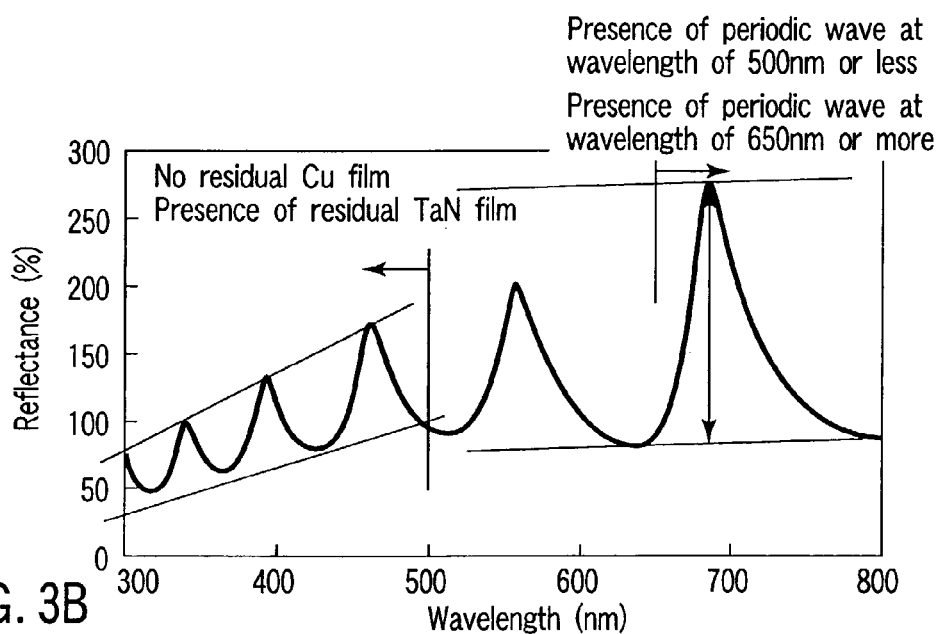
Figure 3C:
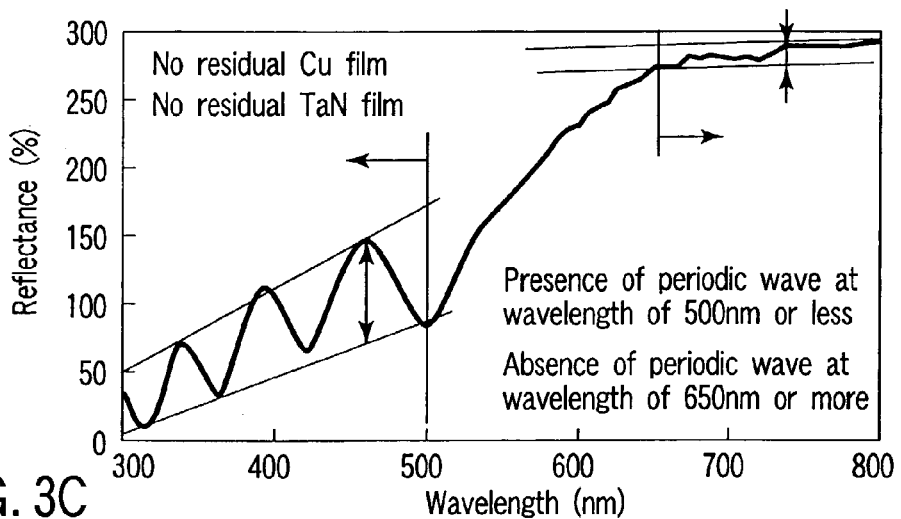

The reflectance spectrum is changed in accordance with progress of the CMP treatment as shown in FIGS. 3A to 3C. Incidentally, the reflectance shown in each of FIGS. 3A to 3C is on the basis that the reflectance of the silicon (Si) substrate is set at 100%.

Stage (a) shows the state that the Cu film 108 on the interlayer insulating film 105 shown in FIG. 1A is so thick that the measuring light is incapable of being transmitted therethrough. In this case, a reflectance similar to that of the Cu bulk is exhibited under the measuring wavelength region, as shown in FIG. 3A. The periodic amplitude cannot be recognized under the wavelength not longer than 500 nm and under the wavelength not shorter than 650 nm.

Stage (b) shows the state that the Cu film 108 is thin enough to permit the measuring light to be transmitted therethrough, or the Cu film 108 is removed. In other words, the Cu film 108 is substantially removed and the TaN film 107 is left unremoved. In this case, the amplitude is present over the entire measuring wavelength region, as shown in FIG. 3B.

Further, stage (c) shows the state that both the Cu film 108 and the TaN film 107 are removed. In this case, the amplitude can be recognized under the wavelength not longer than 500 nm but cannot be recognized under the wavelength not shorter than 650 nm, as shown in FIG. 3C.

In conclusion, the judgment can be made as shown in Table 1 below:

TABLE 1

| Short wavelength side (≦500 nm) periodic wave | Long wavelength side (≧650 nm) periodic wave | Residual Cu film | Residual BM film |
|---|---|---|---|
| none | none | recognized | recognized |
| recognized | recognized | none | recognized |
| recognized | none | none | none |

It should be noted that it is reasonable to judge that, where a periodic wave is not recognized in any of the short wavelength side having a wavelength not longer than 500 nm and the long wavelength side having a wavelength not shorter than 650 nm, both the residual Cu film and the residual BM film are present. Also, where a periodic wave is recognized in each of the short wavelength side having a wavelength not longer than 500 nm and the long wavelength side having a wavelength not shorter than 650 nm, it is reasonable to judge that the residual Cu film is substantially eliminated and the residual BM film is present. Further, where a periodic wave is recognized in the short wavelength side having a wavelength not longer than 500 nm and is not recognized in the long wavelength side having a wavelength not shorter than 650 nm, it is reasonable to judge that both the residual Cu film and the residual BM film are eliminated.

Figure 4:
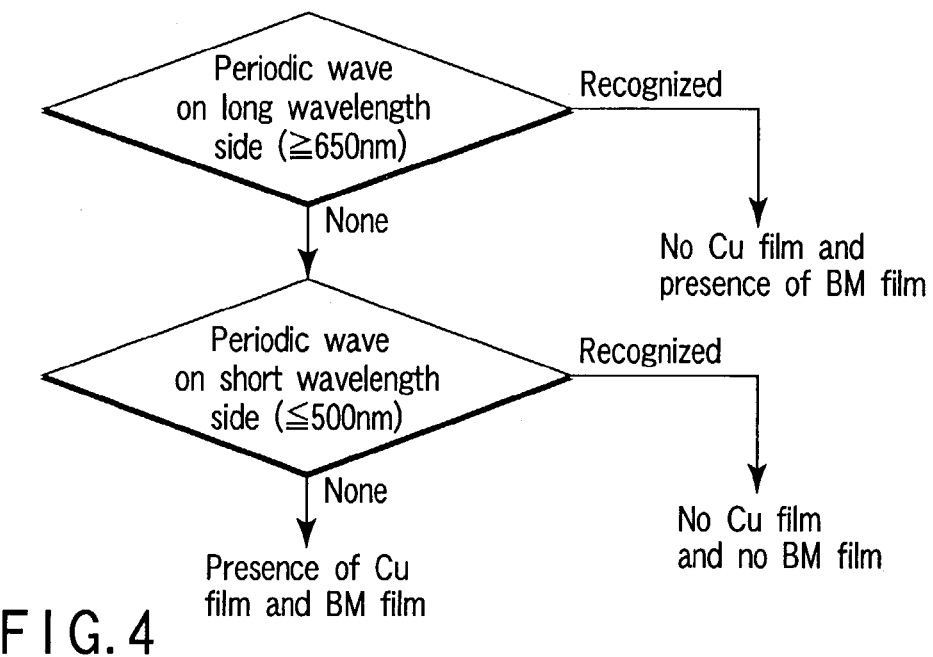
FIG. 4 is a flow chart for judging the residue of the metal film in the CMP treatment.

In this case, it is possible to make a judgment in accordance with the flow chart shown in FIG. 4. Specifically, the presence or absence of the periodic wave on the long wavelength side is judged first. Where there is a periodic wave, it is judged that there is no residual Cu film and there is a residual BM film. Where a periodic wave is not recognized on the long wavelength side, the presence or absence of the periodic wave on the short wavelength side is judged. Where a periodic wave is recognized on the short wavelength side, it is judged that there is no residual Cu film and no residual BM film. Further, where a periodic wave is not recognized on the short wavelength side, it is judged that there are a residual Cu film and a residual BM film.

As described above, it is possible to judge easily the residual Cu film and the residual barrier metal film by using as a criterion of the judgment the periodic wave in a curve obtained by plotting the change in the reflectance relative to the wavelength in the wavelength region on the long wavelength side and the short wavelength side.

Figure 5:
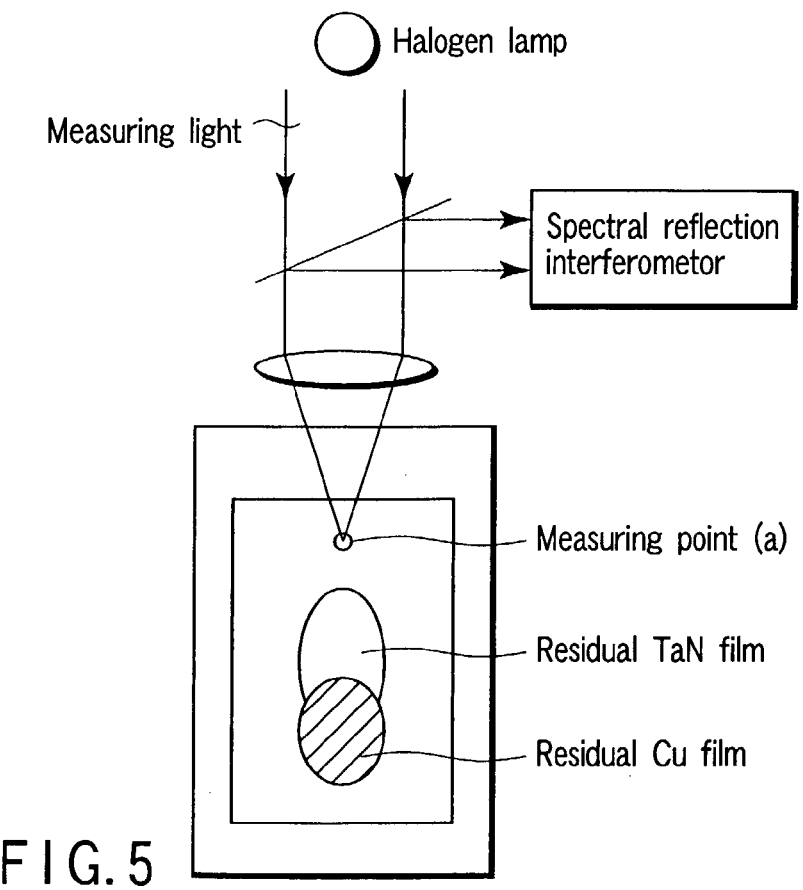
FIG. 5 schematically shows the construction of an apparatus for measuring the residue of the metal film in the CMP treatment.

FIG. 5 schematically shows the construction of an apparatus for judging the residual film after the CMP treatment by the method described above. There is a case where the residual film after the CMP treatment is rendered nonuniform by, for example, the pattern density or the step of the underlying layer. Where there is no Cu residual film and no TaN residual film at a measuring point such as point (a) shown in FIG. 5, it is possible for the residual film to be overlooked. In order to suppress the overlooking of the residual film, it is desirable to carry out the measurement at a plurality of points.

It was customary in the past to judge the residual metal film by obtaining the thickness value of each layer. The film thickness is calculated by the procedure that the spectrum obtained by the calculation, in which the thickness of each layer is changed, is allowed to fit the measured spectrum, and the film thickness value in the case where the spectrum obtained by the calculation is closest to the measured spectrum is employed for judging the residual metal film. It follows that the calculating time is increased with increase in the number of kinds of the films whose thicknesses are obtained and in the range of calculation of the film thickness. Such being the situation, it takes a very long time to calculate the film thickness at a plurality of points by the conventional method of judging the residual film. In the method of judging the residual film in Example 1, however, it suffices to make the judgment based on at least two criteria including the presence or absence of the periodic wave on the long wavelength side and the short wavelength side in the reflectance curve so as to make it possible to eliminate the voluminous calculation required in the conventional method. It should also be noted that, since the determination of an accurate film thickness value is not required for performing the inspection alone of the residual film, the method in Example 1 of the present invention is highly effective in the case of polishing a large region like the CMP treatment, i.e., in judging the residual film in many measuring points.

EXAMPLE 2

The embodiment for Example 2 is directed to an example of measuring in-situ the reflectance during the CMP treatment applied to the Cu film included in the wafer equal in construction to the wafer used in Example 1, i.e., the wafer constructed such that a plurality of films are laminated on a semiconductor substrate.

A CMP apparatus constructed as shown in FIGS. 6A to 6C is used for this method. Specifically, FIG. 6A is an oblique view showing the construction of the CMP apparatus, FIG. 6B is a plan view of the CMP apparatus shown in FIG. 6A, and FIG. 6C is a side cross-sectional view showing the left side portion of the CMP apparatus shown in FIG. 6A.

The CMP apparatus is constructed as follows. Specifically, a polishing pad 603 is arranged on a turntable 601, and a wafer 605 supported by a carrier 607 is arranged such that the surface of the wafer 605 that is to be polished faces downward. A slurry supply nozzle 609 is arranged above the polishing pad 603 such that the wafer 605 is polished by a polishing slurry 606 supplied from the slurry supply nozzle 609. During the polishing treatment, the wafer 605 is irradiated with a measuring light 608, and light reflected from the wafer 605 passes through an optical window 604 formed in the polishing pad 603 so as to be detected by an optical head 602 arranged in a hollow space formed in the turntable 601, thereby measuring the reflectance.

In this method, it is impossible to perform the measurement at a specified site of a prescribed structure on a patterned wafer, and an averaged intensity of the reflected light from the part of the wafer passing over the optical head 602 during the measuring time is obtained as the output. However, in the initial stage of the CMP treatment applied to the Cu film, not only the buried wiring portion but also the field portion are covered with the Cu film. It follows that the entire wafer surface exhibits a reflectance similar to that of a Cu bulk, though there is a slight change in the reflectance caused by the step. Under the circumstances, where the Cu film covers the entire surface of the wafer 605 in the initial stage of the polishing applied to the Cu film, the amplitude of the periodic wave in the reflectance curve relative to the wavelength is made small or the periodic wave is eliminated at the short wavelength not longer than 500 nm and at the long wavelength not shorter than 650 nm as shown in FIG. 3A in conjunction with Example 1, though there is an influence of the scattering by, for example, the polishing slurry 606.

However, if the Cu film in the field portion comes to be eliminated, a periodic wave begins to be observed in the reflectance curve. Although a clear change in the spectrum does not appear, compared with the case of measuring the reflectance on the Cu wiring alone as in Example 1, it is possible to judge depending on the amplitude of the periodic wave in two wavelength regions of the reflectance curve that a Cu film or a barrier metal film is present on the entire surface. Therefore, it is possible to utilize the method of Example 2 for detecting the end point of the polishing.

EXAMPLE 3

Figure 7A:
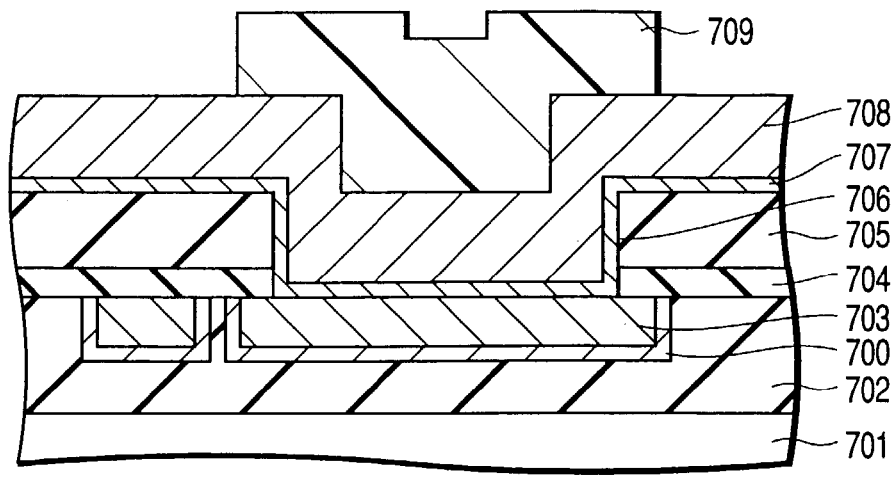
FIGS. 7A to 7C are cross-sectional views for explaining the judgment on the residue of the metal film in forming an aluminum pad above a Cu damascene wiring in Example 3 of the present invention.
Figure 7B:
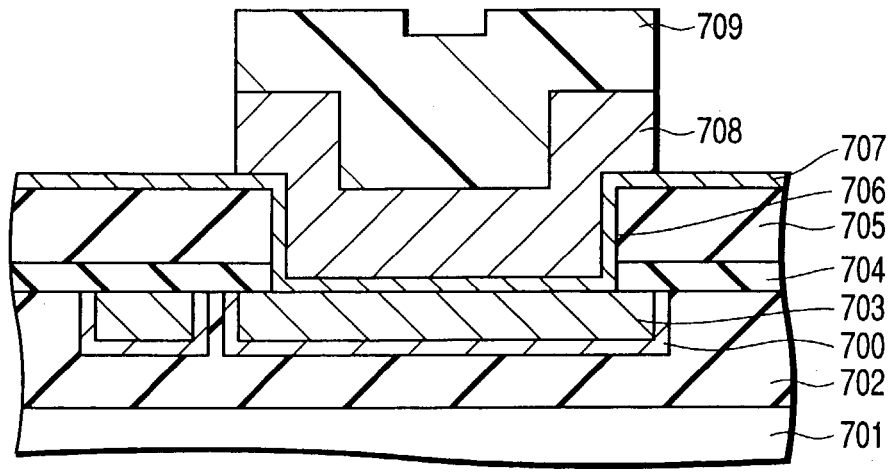
Figure 7C:
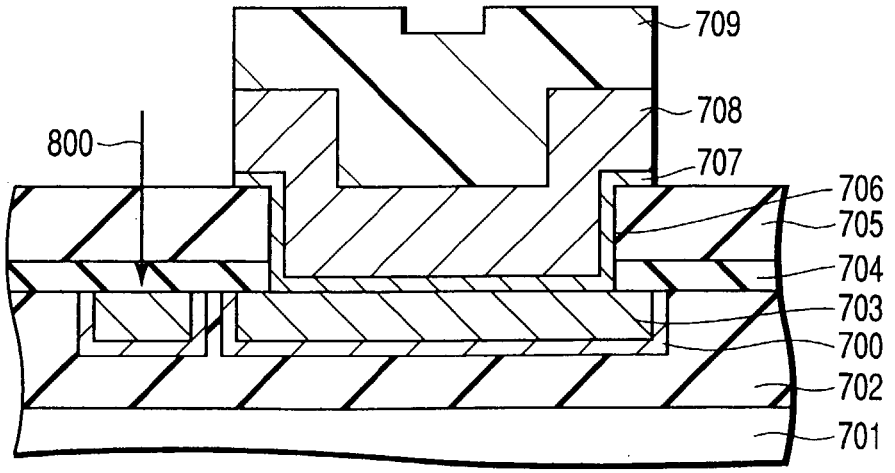

This Example is directed to the formation of an aluminum pad on a copper (Cu) damascene wiring, as shown in FIGS. 7A to 7C. As shown in the drawings, a copper (Cu) buried wiring 703 is formed in an insulating film 702 on a semiconductor substrate 701 having an active element (not shown) formed therein. Also, a tantalum nitride (TaN) liner film 700 is interposed between the copper buried wiring 703 and the insulating film 702. Further, a silicon nitride (SiN) film 704 and a silicon dioxide ($SiO_2$) film 705 constituting an interlayer insulating film are successively formed on the resultant structure, followed by patterning the interlayer insulating film 705 so as to form an opening 706.

In the next step, a tantalum (Ta) film 707 as a barrier metal layer and an aluminum (Al) film 708 are formed on the interlayer insulating film 705 in a manner to fill the opening 706. Then, a resist film is formed on the entire surface, followed by patterning the resist film such that a resist 709 is left in the portion forming an Al pad, as shown in FIG. 7A.

After patterning the resist film, the Al film 708 and the Ta film 707 are selectively removed by a RIE (Reactive Ion Etching) method with the resist 709 used as a mask. In accordance with progress of the RIE treatment, stage (c), in which the Al film 708 and the Ta film 707 are eliminated as shown in FIG. 7C, is reached through stage (a), in which the Al film 708 is left unremoved as shown in FIG. 7A, and stage (b), in which the Al film 708 is eliminated and the Ta film 707 is left unremoved as shown in FIG. 7B.

Figure 8:
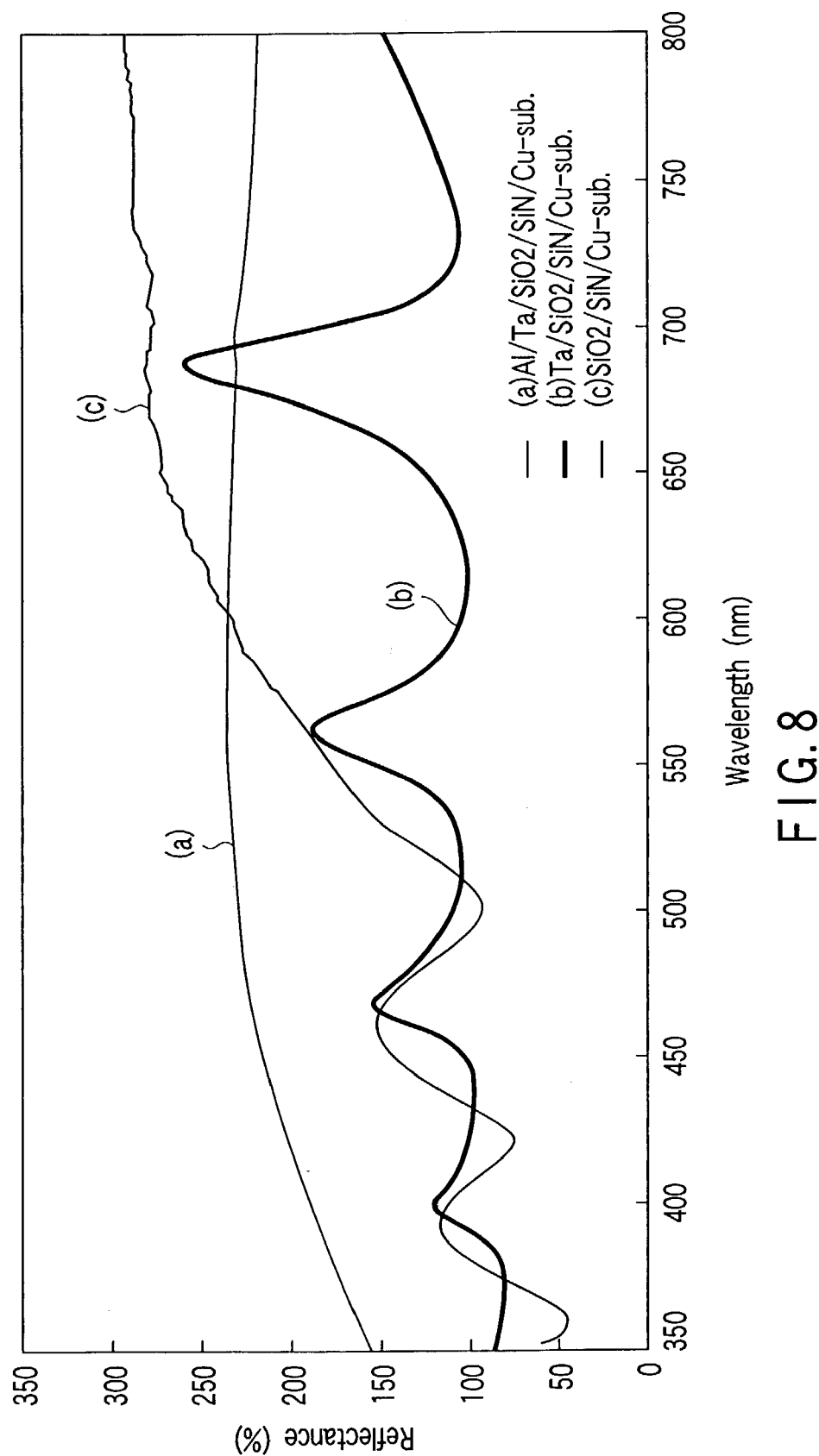
FIG. 8 is a graph showing the reflectance spectrum that is changed with progress in the RIE treatment in forming an Al pad in Example 3 of the present invention.

The interlayer insulating film 705 above the lower layer Cu wiring 703 was irradiated with light 800 so as to measure the reflectance by changing the wavelength within a range of between 350 nm and 800 nm. As a result, three reflectance spectra as shown in FIG. 8 were obtained in accordance with progress of the RIE treatment. It should be noted that the reflectance spectra (a), (b) and (c) shown in FIG. 8 correspond to the stages (a), (b) and (c) referred to above, respectively. Incidentally, the reflectance shown in FIG. 8 is on the basis that the reflectance of the Si substrate is set at 100%.

Stage (a) denotes the state that the Al film 708 is present in a large thickness on the interlayer insulating film 705 and exhibits a reflectance similar to that of an Al bulk in the measuring wavelength region. It is impossible to recognize a periodic wave on the short wavelength side and on the long wavelength side.

Stage (b) denotes the state that the Al film 708 is removed substantially completely and the Ta film 707 is left unremoved. In this case, an amplitude is present over the entire measuring wavelength region.

Further, stage (c) denotes the state that both the Al film 708 and the Ta film 707 are removed substantially completely. In this case, a periodic wave can be recognized in the wavelength region not longer than 500 nm. However, a periodic wave is not recognized in a wavelength region not shorter than 650 nm.

As described above, the residue of the Al film and the barrier metal film can be judged easily in Example 3, too, by application of the flow chart shown in FIG. 4 and Table 1 directed to a judgment table based on the presence or absence of the periodic wave in the reflectance spectrum curve as in Example 1.

As described above in detail, according to embodiments of the present invention, provided is a method of judging the residual film by an optical measurement. The method provided by the embodiments of the present invention produces various merits that the complicated calculation of the optical model is made unnecessary, that a precise optical measurement is made unnecessary, that the judging time can be shortened, and that the judgment of the residual metal film in many points can be performed on the real time basis.

Additional advantages and modifications will readily occur to those skilled in the art. Therefore, the present invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of judging a residual film on a sample by an optical measurement, said sample including a first metal film whose reflectance is changed depending on a wavelength of measuring light, and an insulating film formed above the first metal film, and said residual film being a second metal film above the insulating film, the method comprising:

irradiating the sample with a measuring light so as to measure a change in intensity of light reflected from the sample depending on the wavelength of the measuring light, thereby obtaining a reflectance spectrum curve; and dividing the reflectance spectrum curve into a plurality of wavelength regions so as to judge presence or absence of the second metal film above the insulating film depending on a waveform in each of the wavelength regions of the reflectance spectrum curve, wherein the insulating film is transparent to light having a wavelength falling within a range of the wavelength of the measuring light and has a thickness that permits generating interference depending on the wavelength of the measuring light.

2. A method according to claim 1, wherein the judgment on the presence or absence of the second metal film above the insulating film is performed by allowing presence or absence of a periodic wave, or amplitude of the periodic wave in each of the wavelength regions of the reflectance spectrum curve to correspond to the presence or absence of the second metal film above the insulating film.

3. A method according to claim 1, wherein the first metal is a colored metal selected from the group consisting of Cu and Au.

4. A method according to claim 1, wherein the second metal film is a laminated film of a barrier film and a metal film.

5. A method according to claim 4, wherein the barrier film is selected from the group consisting of a tantalum film, a tantalum nitride film, a titanium film, a titanium nitride film, a tungsten film, a tungsten nitride film, and a laminated film including some of these barrier films.

6. A method according to claim 4, wherein the barrier film has a thickness that permits transmitting light having a wavelength falling within a range of the wavelength of the measuring light.

7. A method according to claim 1, wherein the insulating film is selected from the group consisting of a silicon oxide film, a silicon nitride film, a silicon oxide film containing at least one of fluorine, phosphorus and boron added thereto, an organic insulating film and a laminated film including some of these insulating films.

8. A method of judging a residual film by an optical measurement for judging presence or absence of a barrier film and a metal film above an insulating film of a semiconductor substrate provided with a Cu wiring and the insulating film formed above the Cu wiring, comprising:

irradiating a surface of the semiconductor substrate above the Cu wiring with a measuring light so as to measure a change in intensity of light reflected from the semiconductor substrate depending on a wavelength of the measuring light, thereby obtaining a reflectance spectrum curve; and dividing the reflectance spectrum curve into a plurality of regions including a wavelength region on a side of a short wavelength not longer than 500 nm and a wavelength region on a side of a long wavelength not shorter than 650 nm so as to judge any of three states above the insulating film including (a) substantially presence of the metal film, (b) substantially absence of the metal film and presence of the barrier film, and (c) absence of the metal film and absence of the barrier film, by allowing presence or absence of a periodic wave, or amplitude of the periodic wave on the side of each of the short wavelength and the long wavelength in the reflectance spectrum curve to correspond to the three states given above.

9. A method according to claim 8, wherein, where the periodic wave is not present or the amplitude of the periodic wave is small on each of the short wavelength side and the long wavelength side in the reflectance spectrum curve, situation above the insulating film is judged to be under state (a), where the periodic wave is present or the amplitude of the periodic wave is large on each of the short wavelength side and the long wavelength side in the reflectance spectrum curve, the situation above the insulating film is judged to be under state (b), and where the periodic wave is present or the amplitude of the periodic wave is large on the short wavelength side in the reflectance spectrum curve, and the periodic wave is not present or the amplitude of the periodic wave is small on the long wavelength side in the reflectance spectrum curve, situation on the insulating film is judged to be under state (c).

10. A method according to claim 8, wherein the insulating film is selected from the group consisting of a silicon oxide film, a silicon nitride film, a silicon oxide film containing at least one of fluorine, phosphorus and boron added thereto, an organic insulating film and a laminated film including some of these insulating films.

11. A method according to claim 8, wherein the barrier film is selected from the group consisting of a tantalum film, a tantalum nitride film, a titanium film, a titanium nitride film, a tungsten film, a tungsten nitride film, and a laminated film including some of these barrier films.

12. A method according to claim 8, wherein the barrier film has a thickness that permits transmitting light having a wavelength falling within a range of the wavelength of the measuring light.

13. A method according to claim 8, wherein the insulating film is transparent to light having a wavelength falling within a range of the wavelength of the measuring light and has a thickness that permits generating interference depending on the wavelength of the measuring light.

14. A method of manufacturing a semiconductor device, comprising:
providing a semiconductor substrate including a first metal film whose reflectance is changed depending on the wavelength of a measuring light and an insulating film formed above the first metal film;

depositing a second metal film above the insulating film;

removing selectively the second metal film from a surface of the second metal film gradually;

irradiating a prescribed region of the semiconductor substrate with a measuring light so as to measure a change in intensity of light reflected from the semiconductor substrate depending on the wavelength of the measuring light, thereby obtaining a reflectance spectrum curve; and dividing the reflectance spectrum curve into a plurality of wavelength regions so as to judge presence or absence of the second metal film above the insulating film in a prescribed region depending on a waveform of the reflectance spectrum curve in each of the wavelength regions, thereby detecting an end point in removal of the second metal film, wherein the removal of the second metal film is stopped based on the detected end point so as to finish removing the second metal film, and wherein the insulating film is transparent to light having a wavelength falling within a range of the wavelength of the measuring light and has a thickness that permits generating interference depending on the wavelength of the measuring light.

15. A method according to claim 14, wherein at least one of a groove and a hole is formed in the insulating film, the second metal film is deposited in a manner to fill at least one of the groove and the hole, and the second metal film is gradually removed in a manner to permit the residual second metal film to be buried in at least one of the groove and the hole and to remove that portion of the second metal film which is positioned above the insulating film outside at least one of the groove and the hole.

16. A method according to claim 14, wherein the first metal is a colored metal selected from the group consisting of Cu and Au.

17. A method according to claim 14, wherein the second metal film is a laminated film of a barrier film and a metal film.

18. A method according to claim 14, wherein the insulating film is selected from the group consisting of a silicon oxide film, a silicon nitride film, a silicon oxide film containing at least one of fluorine, phosphorus and boron added thereto, an organic insulating film and a laminated film including some of these insulating films.

* * * * *